United States Patent [19]
Cheng

[11] Patent Number: 5,749,724
[45] Date of Patent: May 12, 1998

[54] DENTAL LIGHT CURING DEVICE

[76] Inventor: Sterling Cheng, No. 226, Kong-Shieh-Sir Village, Chungli, Taiwan

[21] Appl. No.: 854,457

[22] Filed: May 12, 1997

[51] Int. Cl.$^6$ .................................................. A61C 3/00
[52] U.S. Cl. .................................... 433/29; 250/504 H
[58] Field of Search ................. 433/29, 126; 250/504 H

[56] References Cited

U.S. PATENT DOCUMENTS

| | | | |
|---|---|---|---|
| 5,147,204 | 9/1992 | Patten et al. | 433/29 |
| 5,328,368 | 7/1994 | Lansing et al. | 433/29 |
| 5,397,892 | 3/1995 | Abdelqader | 433/29 |
| 5,530,632 | 6/1996 | Shikano et al. | 433/29 |

*Primary Examiner*—John J. Wilson

[57] ABSTRACT

A dental light curing device comprising a casing having a handle integrally formed therewith and extending therefrom to a lower end. The casing is defined by a front cover and a rear casing body. The rear casing body defines an interior space inside which a bulb, serving as a light source, and a reflector substantially concentrically surrounding the bulb are fixed. An optical fiber is mounted to the cover to be positionable in the proximity of the bulb for receiving and guiding light generated from the bulb. A pivotal connection is provided between the front cover and the rear casing body at the lower end of the handle that is far away from the bulb to allow the front cover to be movable relative to the rear casing body between an open position for replacement of the bulb and a closed position. The great distance between the bulb and the pivotal connection allows the optical fiber that is mounted on the front cover to be movable relative to the bulb and the reflector in a approximately linear manner so as to reduce accidental contact between the front cover and the bulb or the reflector.

6 Claims, 4 Drawing Sheets

DENTAL LIGHT CURING DEVICE

FIELD OF THE INVENTION

The present invention relates to a dental light curing device and in particular to an improved dental light curing device which prevents the fiber optic from being accidentally damaged during the replacement of a broken bulb of the device.

BACKGROUND OF THE INVENTION

In the decayed tooth restoration, doctors place a light-curable filling material at the decayed area of the tooth and then cure the filling material with light to restore the tooth. To cure the filling material, a light curing device is used to project light to the filling material to facilitate curing the filling material.

The dental light curing device comprises a light generation device within which a bulb serving as a light source for the generation of the curing light is disposed. Usually, the bulb has a service life of approximately 20–25 hours and thus has to be replaced frequently. The dental light curing device also comprises an optic fiber which is mounted to the light generation device at such a position to guide the light from the bulb to the filling material for curing the filling material.

An example of the prior art dental light curing device is shown in FIG. 1 of the accompanying drawings, wherein the dental light curing device comprises a light generation device 1 constituted by a casing 10 defining therein an interior space 101 for receiving and holding a light source, such as a bulb 102 centered within a reflector 103. The casing 10 has a threaded opening 12 to which a cap or cover 11 having an interior threading 111 is threadingly mounted. A handle 109 extends from the casing 10 for hand holding. The cap 11 has an opening for receiving and holding therein an optical fiber 2 so as to allow the light generated by the bulb 102 to be guided by the optical fiber 2. The optical fiber 2 has an connecting section 23 on which a circumferential groove 24 is provided to be engaged by a spring clip 112 mounted inside the cap 11 so as to fix the optical fiber 2 to the cap 11.

The threading engagement between the cap 11 and the casing 10 allows the cap 11 to be detached from the casing 10 for replacement of the bulb 102. In replacing the bulb 102, the cap 11, together with the optical fiber 2 mounted thereon, is completely separated from the casing 10 and temporarily placed on for example a desk (not shown). An accidental touch of the cap 11 that is placed on the desk during the replacement of the bulb 102 may sometimes cause the cap 11 to fall off the desk and thus damaging the optical fiber 2 which is, in general, the most valuable parts of the light curing device.

To solve such a problem, attempts have been made to provide a dental light curing device in which the cap is rotatably mounted to the casing by means of a pivot located at the edge of the opening of the casing so that when the cap is released from the casing, the cap is still connected to the casing and thus prevent the optical fiber from being damaged due to an accidental fall. Such an arrangement, however, has a disadvantage that, after the bulb is replaced, in resecuring the cap to the casing, the rotation of the cap relative to the casing may cause an accidental contact between the cap and the bulb reflector, due to the short rotation radius provided between the pivot and the bulb, which may slightly displaces the reflector so as to have the effectiveness of the dental light curing device deteriorate.

It is therefore desirable to provide an improved dental light curing device which overcomes the accidental contact problem encountered in the prior art design.

SUMMARY OF THE INVENTION

The principal object of the present invention is therefore to provide a dental light curing device comprising a front cover section and a rear casing body section pivoted to each other with the pivotal connection being remote from the bulb so as to reduce accidental contact between the front cover section and the bulb caused by arc movement of the cover section relative to the casing section in re-mounting the cover section to the rear casing body section.

In accordance with the present invention, to achieve the above and other objects of the present invention, there is provided a dental light curing device comprising a casing having a handle integrally formed therewith and extending therefrom to a lower end. The casing is defined by a front cover and a rear casing body. The rear casing body defines an interior space inside which a bulb, serving as a light source, and a reflector substantially concentrically surrounding the bulb are fixed. An optical fiber is mounted to the cover to be positionable in the proximity of the bulb for receiving and guiding light generated from the bulb. A pivotal connection is provided between the front cover and the rear casing body at the lower end of the handle that is far away from the bulb to allow the front cover to be movable relative to the rear casing body between an open position for replacement of the bulb and a closed position. The great distance between the bulb and the pivotal connection allows the optical fiber that is mounted on the front cover to be movable relative to the bulb and the reflector in a approximately linear manner so as to reduce accidental contact between the front cover and the bulb or the reflector.

BRIEF DESCRIPTION OF THE DRAWINGS

The present invention will be better understood from the following description of a preferred embodiment thereof, with reference to the attached drawings, wherein.

DETAILED DESCRIPTION OF THE PREFERRED EMBODIMENT

Figure 1:
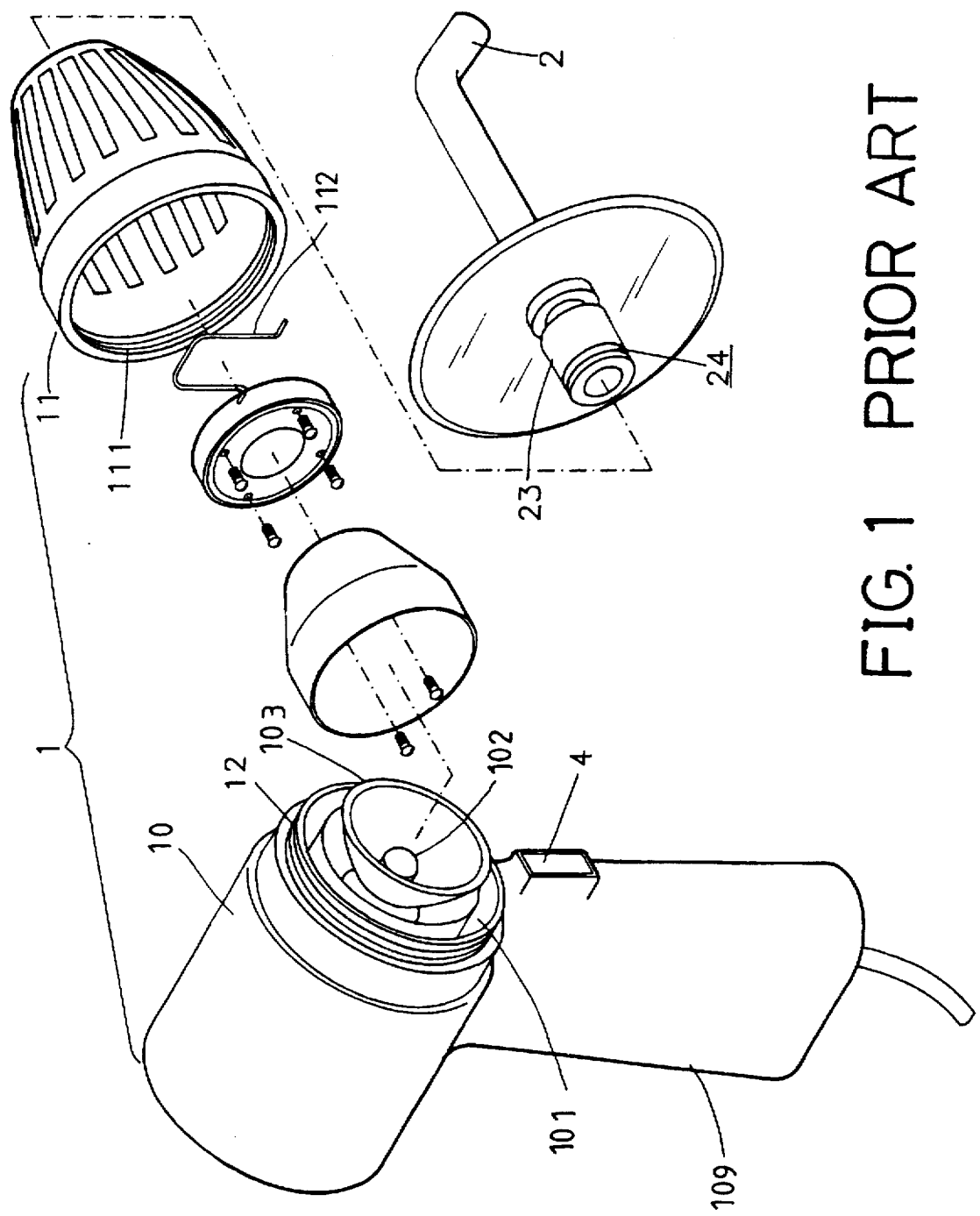
FIG. 1 is an exploded perspective view showing a prior art dental light curing device.
Figure 2:
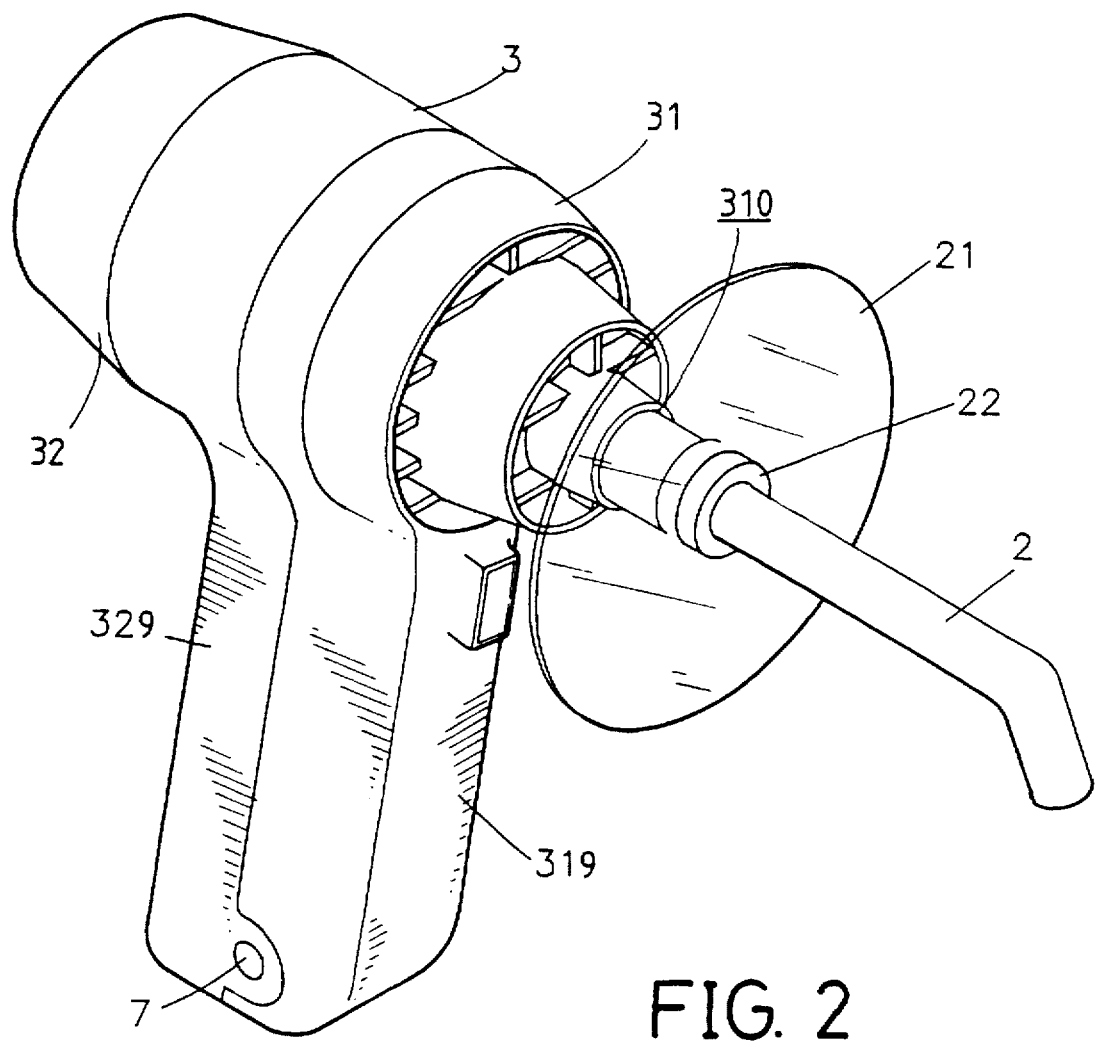
FIG. 2 is a perspective view showing a dental light curing device constructed in accordance with the present invention.
Figure 3:
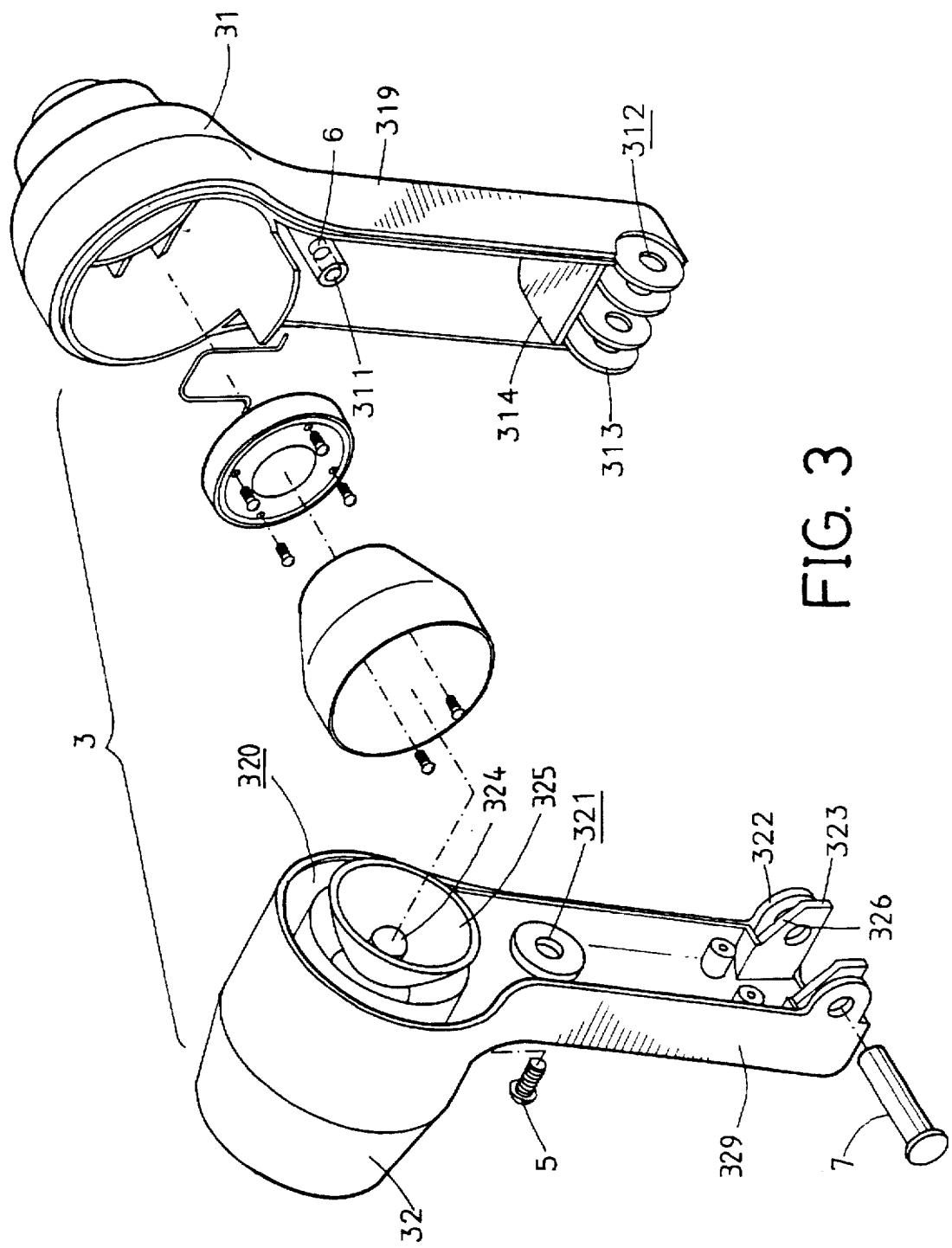
FIG. 3 is an exploded perspective view of the dental light curing device in accordance with the present invention.
Figure 4:
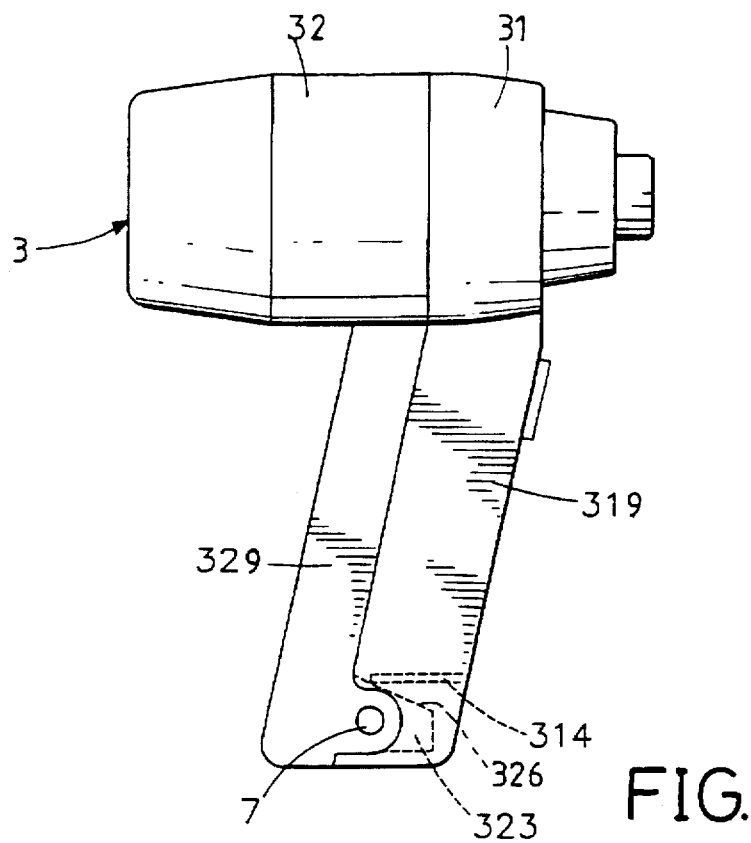
FIG. 4 is a side elevational view of the dental light curing device of the present invention showing the front cover is at the closed position and secured to the casing and thus ready for use.

With reference to the drawings and in particular to FIGS. 2 and 3, a dental light curing device constructed in accordance with the present invention is shown, comprising a device housing 3 having a front cover 31 and a rear casing body 32, each having a handle portion 319 and 329 preferably integrally formed therewith and extending therefrom to define a lower end on which a pivotal connection is formed to pivot the cover 31 to the casing body 32 which allows the cover 31 to be rotatable with respect to the casing body 32 between an open position (FIG. 5) where the cover 31 is away from the casing body section 32 and a closed position (FIG. 4) where the cover 31 engages the casing body 32.

The casing body 32 defines an interior space 320 at a location opposite to and thus away from the pivotal connection. A bulb 324, serving as a light source, is fixed within the interior space 320 and concentrically surrounded by a reflector 325, to provide a light beam in a direction toward the cover 31.

The cover 31 is provided with an opening 310 (see FIG. 2) through which an optical fiber 2 is received and fixed to have an inner end of the optical fiber 2 to be positionable in the proximity of the bulb 324 at the closed position so as to receive light beam from the bulb 324.

The pivotal connection between the cover 31 and the casing body 32 comprises two pairs of spaced walls 313 formed on the lower end of the cover 31 and two lugs 323 formed on the casing body 32 to be received within the spacings between the two pairs of walls 313. Both the walls 313 and the lugs 323 have a central hole through which a pivot pin 7 extends to complete the pivotal connection.

Figure 5:
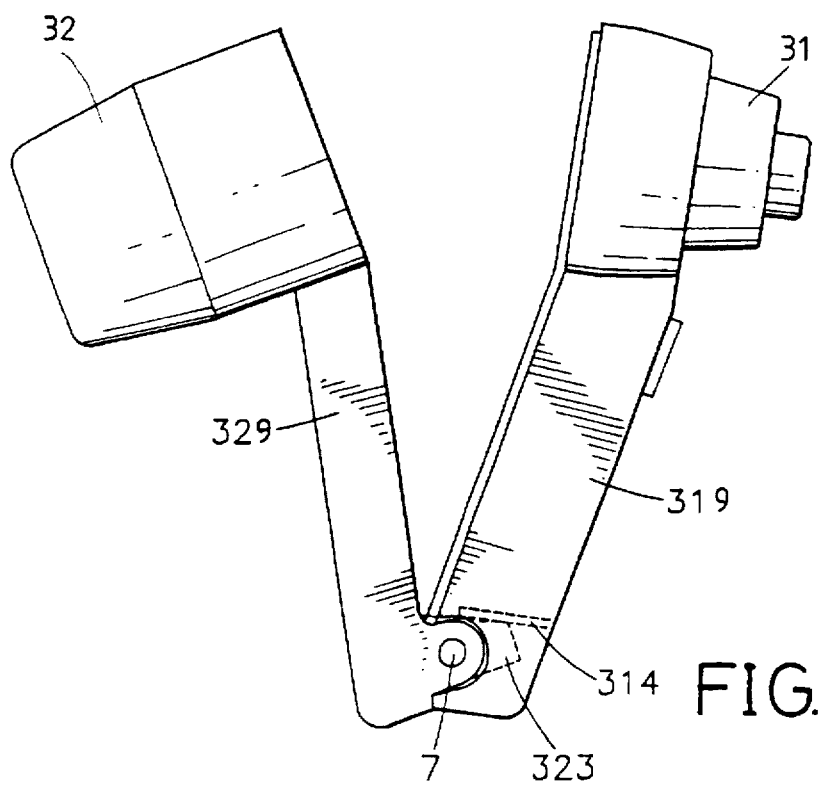
FIG. 5 is a side elevational view of the dental light curing device of the present invention showing the front cover is at the open position and separated from the casing body for replacement of the bulb.

The lugs 323 are provided with an engaging edge 326 which is engageable with a stop plate 314 fixed on the cover 31 when the cover 31 is at the open position so as to fix the cover 31 at the open position relative to the casing body 32, as shown in FIG. 5.

Preferably, the casing body 32 is provided with a side lug 322 at the lower end thereof and located outboard of and spaced from each of the inner lug 323 to be fit within a corresponding recess 312 formed on the cover 31 and receive one of the walls 313 of each of the two pairs between the side lug 322 and the associated inner lug 323. Preferably, the side lugs 322 are extensions of the casing wall of the casing body 32 and the recesses 312 are formed on the outside wall of the cover 31 so that when the side lugs 322 are received within the recesses 312, a smooth outer surface of the housing 3 is defined when the cover 31 is at the closed position (FIG. 5).

Arranging the pivotal connection at the lower end of the handle (319 and 329) of the dental light curing device significantly increases the distance between the bulb 324 and the pivot pin 7 so that the movement of the inner end of the optical fiber 2 relative to the bulb 324 is more close to a linear translation which allows the optical fiber 2 to be more precisely aligned with the bulb 324 and thus accidental contact between the optical fiber 2 (or the cover 31) and the bulb 324 (or the reflector 325) may be reduced.

Securing means may be provided to secure the cover 31 at the closed position relative to the casing body 32. The securing means may be any known device, such as a bolt 5 shown in the drawings, which bolt 5 extends through a hole 321 formed on the casing body 32 and threadingly engages a nut 6 received and fixed inside a bore 311 formed on the cover 31.

Although a preferred embodiment has been described to illustrate the present invention, it is apparent that changes and modifications in the specifically described embodiment can be carried out without departing from the scope of the invention which is intended to be limited only by the appended claims.

What is claimed is:

1. A dental light curing device comprising a housing having a first casing member and a second casing member, the second casing member being matingly engageable with the first casing member to define the housing, the first casing member having an interior space for receiving and fixing therein a light source, the second casing member having an optical fiber mounted thereon to have an inner end of the optical fiber positioned in the proximity of the light source to receive light therefrom, each of the first and second casing members having an elongated extension formed therewith and matingly engageable with each other, each of the extensions having a lower end with a pivotal connection provided thereon so as to allow the second casing member to be rotatable about the pivotal connection with respect to the first casing member between a closed position where the casing members and the extensions thereof engage each other and an open position where the second casing member is away from the first casing member.

2. The dental light curing device as claimed in claim 1, further comprising securing means for securing the second casing member at the closed position relative to the first casing member.

3. The dental light curing device as claimed in claim 2, wherein the securing means comprises a bolt extending between the first and second casing members and tightened by a nut.

4. The dental light curing device as claimed in claim 1, wherein the pivotal connection comprises two pairs of walls formed on the lower end of the second casing member and an inner lug provided on the lower end of the first casing member to be corresponding to and received between each pair of the walls of the second casing member, each of the walls and the inner lugs having a through hole to receive a pivot pin extending therethrough.

5. The dental light curing device as claimed in claim 4, wherein the inner lugs have an engaging edge which is brought into contact engagement with a stop plate fixed on the second casing member when the second casing member is moved from the closed position to the open position so as to fixed the second casing member at the open position relative to the first casing member.

6. The dental light curing device as claimed in claim 4, wherein the pivotal connection further comprises two side lugs provided on the lower end of the first casing member, each located outboard of a respective one of the inner lugs and spaced therefrom to receive an outer one of the walls of each of the pairs, each of the side lugs being movably received within a recess formed on side walls of the second casing member so as to provide a smooth outer surface of the housing when the second casing member is at the closed position.

* * * * *